United States Patent [19]

Shigematsu et al.

[11] 4,166,846
[45] Sep. 4, 1979

[54] CHEMICALS FOR CONTROLLING PLANT VIRUS DISEASES AND CONTROL METHOD

[75] Inventors: Taichiro Shigematsu, Machida; Hiroshi Kasugai, Hino; Tetsuya Shibahara, Miho; Tetsuo Nakajima, Kawasaki; Toru Teraoka, Yokohama, all of Japan

[73] Assignee: Mitsubishi Chemical Industries, Ltd., Tokyo, Japan

[21] Appl. No.: 923,991

[22] Filed: Jul. 12, 1978

[30] Foreign Application Priority Data

Aug. 16, 1977 [JP] Japan ............................... 52-98044
May 4, 1978 [JP] Japan ............................... 53-53424

[51] Int. Cl.$^2$ ............................................. A01N 9/00
[52] U.S. Cl. ........................................ 424/81; 424/78; 424/311; 424/314
[58] Field of Search ............... 424/81, 311, 314, 78

[56] References Cited

U.S. PATENT DOCUMENTS

| 3,338,939 | 8/1967 | Harrison | 424/314 |
| 3,749,769 | 7/1973 | Sugiyama et al. | 424/81 |
| 3,910,971 | 10/1975 | Hunsucker | 424/311 |

*Primary Examiner*—V. D. Turner
*Attorney, Agent, or Firm*—Lane, Aitken & Ziems

[57] ABSTRACT

Chemicals containing an effective amount of homopolymers of dialkylaminoalkyl acrylate derivatives or dialkylaminoalkyl methacrylate derivatives or copolymers of such derivatives with ethylenically unsaturated monomers copolymerizable therewith. The chemicals exhibit a remarkable effect of preventing agricultural plants from being infected with plant virus diseases. A method for controlling the plant virus diseases is also described.

18 Claims, No Drawings

CHEMICALS FOR CONTROLLING PLANT VIRUS DISEASES AND CONTROL METHOD

BACKGROUND OF THE INVENTION

1. Field of the Invention

This invention relates to chemicals for controlling plant virus diseases and also to a control method using such chemicals.

2. Description of the Prior Art

It is known that the plants such as tobacco, tomato, Spanish paprika, potato, cowpea, French bean, cucumber, water melon, strawberry, melon, Chinese cabbage, radish and the like, which are cultivated in various manners of culture such as fieled culture, glasshouse culture, etc., tend to suffer from mosaic diseases and dwarfing diseases to plant viruses such as a tobacco mosaic virus (hereinlater abbreviated as TMV), cucumber mosaic virus (hereinlater abbreviated as CMV), cucumber green mottle mosaic virus (hereinlater abbreviated as CGMMV), potato virus X (hereinlater abbreviated as PVX), lettuce mosaic virus (hereinlater abbreviated as LMV), melon necrotic spot virus (hereinlater abbreviated as MNSV) and the like, thus frequently incurring a great deal of damage to these plants. Since these plant viruses generally exist in various plants, weeds, seeds, soils, roots remaining in soil, the plant suffers readily contagion to the viruses by the suction of plant juice by the insects, by artificial contact (such as with farm appliances, hand, or clothes), or by the contact with the virus-containing soil during transplantation or planting, etc. If a primary contagion takes place, there is a danger that the plant virus spreads throughout the field or other culture systems by the artificial contact such as the farming work.

Various chemicals for controlling such plant virus diseases are known including: antibiotics and base in nucleic acid-like substances both of which have a function of suppressing multiplication of plant viruses; and the juices of plants such as dyer's grape (*Phytaracca decandra*), goosefoot, carnation, etc., and polymeric materials derived from living body such as casein, alginic acid, etc both of which have a function of preventing contagion of plant viruses to the plants. However, most of the former substances exhibit toxicity against man and domestic animals as well as plants and thus have never been used in practical application. The latter substances are of natural origin and thus a difficulty is encountered in mass-producing the substances having uniform composition. Only one instance which has been practically used is a chemical containing sodium alginate as a principal component (wettable powder of alginic acid: Registration No. 13440 at the Minister of the Agriculture and Forestry, Japan).

Therefore, if a plant has been once infected with a disease in the culture field, the secondary contagion is generally prevented by a passive manner that the infected plants are removed and burnt up as soon as we find.

We have made an intensive study to develop an agricultural chemical for controlling plant virus diseases which is innoxious and high in efficacy and, as a result, found that polymers of dialkylaminoalkyl acrylate derivatives or dialkylaminoalkyl methacrylate derivatives show high activity of controlling plant virus diseases.

SUMMARY OF THE INVENTION

Thus, an object of the present invention is to provide an agricultural chemical for plant virus control which is innoxious and high in control efficacy.

Another object of the invention is to provide a control method using the chemical of the just-mentioned type.

According to the present invention, these objects are attained. This invention relates to a chemical for controlling plant virus diseases which containing an effective amount of a homopolymer of a compound expressed by the general formula:

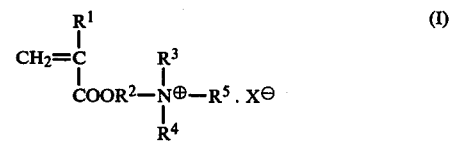

(wherein $R^1$ represents a hydrogen atom or a methyl group, $R^2$ represents a linear or a branched alkylene group containing from 2 to 5 carbon atoms, $R^3$ and $R^4$ independently represents a lower alkyl group, $R^5$ represents a hydrogen atom or a lower alkyl group, and X represents a halogen atom, an acid radical or a lower alkylsulfuric acid radical) or a copolymer of the compound of formula (I) with at least one copolymerizable ethylenically unsaturated monomer, and relates to a control method using the chemical.

DETAILED DESCRIPTION OF THE INVENTION

According to the present invention, there is used a polymeric substance of the compound having the general formula (I) above described as an effective component to control plant virus diseases.

In a compound the general formula (1), $R^1$ represents a hydrogen atom or a methyl group; $R^2$ represents a linear or a branched alkylene group containing from 2 to 5 carbon atoms, preferably dimethylene, trimethylene, tetramethylene group or ethylene group having at least one side chain methyl group, such as iso-propyl group, tert-butyl group; $R^3$ and $R^4$ may be same or different, represent a lower alkyl group, preferably an alkyl group containing from 1 to 3 carbon atoms, concretely a methyl group, a ethyl group or a propyl group; $R^5$ represents a hydrogen atom or a lower alkyl group, preferably a hydrogen atom or a alkyl group containing from 1 to 3 carbon atoms, concretely a methyl group, a ethyl group or a propyl group; X represents a halogen atom such as a chlorine atom, a bromine atom and an iodine atom, an inorganic acid radical such as $NO_3$ and $\frac{1}{2}(SO_4)$, a lower fatty acid radical such as HCOO, $CH_3COO$ and $C_2H_5COO$ or a lower alkyl sulfuric acid radical such as $CH_3SO_4$ and $C_2H_5SO_4$, preferably a chlorine atom, a bromine atom, an iodine atom, an inorganic acid radical, a fatty acid radical containing from 1 to 3 carbon atoms or an alkyl sulfuric acid radical containing from 1 to 3 carbon atoms in the alkyl moiety thereof. In case of $R^5$ is a hydrogen atom, X is selected from a halogen atom, a inorganic acid radical and a lower fatty acid radical, and in case of $R^5$ is an alkyl group, X is selected from a halogen atom and a lower alkyl sulfuric acid radical.

The following are examples of dialkylaminoalkyl acrylate derivatives or dialkylaminoalkyl methacrylate derivatives according to formula (I), dimethylamino(α-methyl)ethyl methacrylate hydrochloride, dimethylamino(β-dimethyl)ethyl methacrylate acetate, dimethylaminotrimethyl methacrylate sulfate, dimethylammonium (β-dimethyl)ethyl methacrylate methylsulfate, dimethylammonium(β-dimethyl)ethyl methacrylate bromide, diethylammonium(α-methyl)ethyl methacrylate chloride, dimethylammoniumethyl acrylate methylsulfate, dimethylaminoethyl methacrylate hydrochloride.

It is known that the compound of formula (I) can be prepared by either quaterizing a compound expressed by the general formula (II)

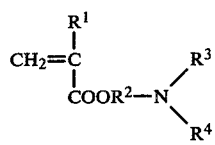

(wherein $R^1$, $R^2$, $R^3$ and $R^4$ have the same meanings as defined in the foregoing formula (I), respectively) with an alkyl halide such as methyl chloride, methyl bromide, methyl iodide, ethyl bromide or the like or with an alkylsulfuric acid such as dimethylsulfuric acid or diethylsulfuric acid, or neutralizing the compound of formula (II) with an acid such as hydrochloric acid, sulfuric acid, nitric acid, sulfamic acid or acetic acid.

The preparation of the polymer, an effective component of the chemical according to the invention, from the compound of formula (I) is feasible by any of known techniques. For instance, the polymer can be obtained by subjecting to polymerize the compound of formula (I) alone or in combination with at least one copolymerizable ethylenically unsaturated monomer in the manner of a precipitation or a suspension polymerization in the presence of a catalyst for the polymerization. Examples of the ethylenically unsaturated monomers copolymerizable with the compound of formula (I) include nonionic monomers such as lower alkyl esters of unsaturated carboxylic acids, i.e., methylacrylate, ethylacrylate, methylmethacrylate and the like, acrylamide, methacrylamide, vinylpyrrolidone, acrylonitrile, methacrylonitrile, vinylacetate, vinyl methyl ether, vinyl ethyl ether, ethylene, isobutylene and the like, cationic monomers such as vinyl pyridines, p-dimethylaminomethylstyrene and the like. Of these, acrylamide and methacrylamide are preferred.

When a copolymer is used as the effective component of the chemical of the invention, the content of the compound of formula (I) in the copolymer should be within a range of above 10 mol %, preferably above 30 mol %.

A polymer and copolymer of this invention are water-soluble or water-suspensible, preferably water-soluble. Therefore, when the ethylenically unsaturated monomers in the copolymer are water-insoluble, the rate of said monomer in a compound limited within a rage of from 1 to 20 mol %.

The intrinsic viscosity of polymers may be within a rage of from 0.3 to 15.

The polymer or copolymer described above may be used, as it is, as the control agent but is generally admixed with adjuvants to use in the form of a wettable powder, a dust, an emulsion or a solution.

In the case of the dust, a carrier and a surface active agent are employed to mix with the polymer. Suitable examples of the carrier include kaolin, bentonite, talc, clay, white carbon and diatomaceous earth. These carriers may be used singly or in combination.

When using in the form of a wettable powder, the surface active agents are employed so as to improve the dispersiveness of the chemical in water and to increase the extend effect when sprayed on plants. (In this specification, the wettable powder means that which does not contain the carriers.) A wide variety of surface active agents including nonionic active agents and cationic active agents are usable for this purpose. Suitable agents include nonionic active agents such as polyoxyethylene alkylallyl ether, polyoxyethylene sorbitan monoalorate, etc. These agents may be used singly or in combination, which depends on the purpose in end use of the wettable powder.

Further, when the chemical is used as an emulsion or solution, water and/or a solvent miscible with water is employed aside from the above-mentioned two types of adjuvants. Such solvents include alcohols such as methyl alcohol, ethyl alcohol and ethylene glycol, ketones such as acetone, ether such as dioxane and tetrahydrofuran, amides such as dimethylformamide, and a mixture thereof.

When the polymer is applied as the control agent in the form of a wettable powder, 70–99 parts by weight of the polymer and 1–30 parts by weight of a surface active agent are mixed in a suitable ratio. In application, the mixture is diluted with water to have a desired concentration and applied for the control.

To apply the polymer in the form of an emulsion or solution, 10–60 parts by weight of the polymer, 20–90 parts by weight of a solvent and 1–20 parts by weight of a surface active agent are mixed in desired ratios. Then, the mixture is applied by dilution with water similarly to the case of the wettable powder.

In the case of the dust, 1–20 parts by weight of the polymer, 80–98 parts by weight of a carrier and 1–5 parts by weight of a surface active agent are uniformly mixed in desired ratios and applied.

The chemical for the plant virus disease control according to the invention can effectively control an contagion of viruses such as TMV, CMV, CGMMV, etc., by soil treatment or by spraying on stems and leaves of growing plants. With the case of the wettable powder, emulsion or solution, a solution having a concentration of the effective component ranging 500–5000 ppm is sprayed on plants or irrigated into soils in an amount of 50–3000 l per 10 ares. With the dust, it is admixed with soils in an amount of 300–10000 g/10 ares as effective component.

As a matter of course, the polymer may be used by mixing with other active components which do not impede the antiviral activity of the polymer, e.g., fungicide, insecticide, miticide, etc.

The chemicals of the invention are effective to the mosaic diseases by the following viruses, TMV, CMV, CGMMV, PVX, LMV, MNSV and the like, especially, TMV, CMV and CGMMV.

The chemicals of this invention are effective to prevent the virus deseases from spreading over the plants belong to Solanaceae, Cucurbitaceae, Luguminosae, Rosaceae and Cruciferae, concretely, tobacco, tomato, Spanish paprika, potato, cucumber, melon, watermelon, cowpea, French bean, radish, Chinese cabbage, strawberry and the like, especially, Solanaceae such as tobacco, tomato and Spanish paprika, and Cucurbitaceae such as cucumber, watermelon and melon.

The present invention will be particularly described by way of the following examples showing preparations of polymers and experiments of the chemicals using such polymers as effective component. These examples are for purposes of exemplification only and in no way are intended to limit the scope of the invention.

PREPARATIVE EXAMPLE 1

4.94 g of dimethylamino(α-methyl)ethyl methacrylate, and 10.04 g of water were introduced into a test tube, to which was added 3.02 g of 35% concentrated hydrochloric acid under agitation to obtain an aqueous hydrochloride solution.

Then, 2.0 g of an aqueous 1% ammonium persulfate solution was added to the aqueous solution and, after degassing, nitrogen gas was charged into the reaction system, followed by polymerization at 60° C. for 3 hours. Thereafter, acetone was added to the reaction system to precipitate a gel, followed by a decantation and a removal of acetone and water thereby obtaining a polymer of the hydrochloride of dimethylamino(α-methyl)ethyl methacrylate (compound No.1).

The above process was repeated using various salts of methacrylate derivatives and acrylate derivatives to obtain polymers (compound Nos. 2-14, 16-23 and 26).

The structural formulae and intrinsic viscosities of these compounds (Nos. 1-14, 16-23 and 26) are indicated in Table 1.

In Table 1, n and m independently represent a natural number.

Preparative Example 2

1.23 g of dimethylaminopropyl methacrylate and 33.51 g of water were introduced into a test tube, to which was further added 0.75 g of 35% concentrated hydrochloric acid under agitation to obtain an aqueous hydrochloride solution.

To the aqueous solution were added 0.51 g of acrylamide and 2.0 g of an aqueous 1% ammonium persulfate and, after degassing, the system was filled with nitrogen gas, followed by copolymerization at 60° C. for 3 hours. After completion of the copolymerization, acetone was added to the reaction system to precipitate a gel, followed by a decantation and a removal of acetone and water to obtain a copolymer (compound No. 15).

The above process was repeated using different starting materials to obtain a copolymer of a hydrochloride of dimethylaminoethyl methacrylate and acrylamide (compound No. 24) and a copolymer of a hydrochloride of dimethylaminoethyl methacrylate and vinylpyridine (compound No. 25).

The structural formulae and intrinsic viscosities of these compounds (Nos. 15, 24 and 25) are indicated in Table 1 below.

Table 1

| Compound No. | Structural Formula | Intrinsic* Viscosity | Remarks |
|---|---|---|---|
| 1 | $-(CH_2-C(CH_3))_n-CO_2CH(CH_3)-CH_2N^{\oplus}(CH_3)_2-H\ Cl^{\ominus}$ | 0.98 | |
| 2 | $-(CH_2-C(CH_3))_n-CO_2CHCH_2N^{\oplus}(CH_3)_2-H\ CH_3COO^{\ominus}$ (with CH₃ on CH) | 0.80 | |
| 3 | $-(CH_2-C(CH_3))_n-CO_2CHCH_2N^{\oplus}(CH_3)_2-H\ \frac{1}{2}(SO_4^{\ominus\ominus})$ (with CH₃ on CH) | 1.07 | |
| 4 | $-(CH_2-C(CH_3))_n-CO_2CH_2C(CH_3)_2-N^{\oplus}(CH_3)_2-H\ Cl^{\ominus}$ | 1.65 | |
| 5 | $-(CH_2-C(CH_3))_n-CO_2CH_2C(CH_3)_2-N^{\oplus}(CH_3)_2-H\ CH_3\ COO^{\ominus}$ | 1.26 | |
| 6 | $-(CH_2-C(CH_3))_n-CO_2CH_2CH_2CH_2N^{\oplus}(CH_3)_2-H\ Cl^{\ominus}$ | 1.15 | |

Table 1-continued

| Compound No. | Structural Formula | Intrinsic* Viscosity | Remarks |
|---|---|---|---|
| 7 | $\text{\textemdash(CH}_2\text{\textemdash C(CH}_3\text{))}_n\text{\textemdash CO}_2\text{CH}_2\text{CH}_2\text{CH}_2\text{N}^\oplus(\text{CH}_3)_2\text{\textemdash H Cl}^\ominus$ | 0.82 | |
| 8 | $\text{\textemdash(CH}_2\text{\textemdash C(CH}_3\text{))}_n\text{\textemdash CO}_2\text{CH}_2\text{CH}_2\text{CH}_2\text{N}^\oplus(\text{CH}_3)_2\text{\textemdash H } \tfrac{1}{2}(\text{SO}_4^{\ominus\ominus})$ | 1.95 | |
| 9 | $\text{\textemdash(CH}_2\text{\textemdash C(CH}_3\text{))}_n\text{\textemdash CO}_2\text{CH}_2\text{C(CH}_3\text{)}_2\text{\textemdash N}^\oplus(\text{CH}_3)_2\text{\textemdash CH}_3\text{ CH}_3\text{SO}_4^\ominus$ | 1.23 | |
| 10 | $\text{\textemdash(CH}_2\text{\textemdash C(CH}_3\text{))}_n\text{\textemdash CO}_2\text{CH}_2\text{CH}_2\text{CH}_2\text{N}^\oplus(\text{CH}_3)_2\text{\textemdash CH}_3\text{ CH}_3\text{SO}_4^\ominus$ | 1.24 | |
| 11 | $\text{\textemdash(CH}_2\text{\textemdash C(CH}_3\text{))}_n\text{\textemdash CO}_2\text{CH}_2\text{C(CH}_3\text{)}_2\text{\textemdash N}^\oplus(\text{CH}_3)_3\text{ Br}^\ominus$ | 1.77 | |
| 12 | $\text{\textemdash(CH}_2\text{\textemdash C(CH}_3\text{))}_n\text{\textemdash CO}_2\text{CH}_2\text{C(CH}_3\text{)}_2\text{\textemdash N}^\oplus(\text{CH}_3)_3\text{ Cl}^\ominus$ | 1.00 | |
| 13 | $\text{\textemdash(CH}_2\text{\textemdash C(CH}_3\text{))}_n\text{\textemdash CO}_2\text{CH}_2\text{CH}_2\text{CH}_2\text{N}^\oplus(\text{CH}_3)_2\text{\textemdash CH}_3\text{ Cl}^\ominus$ | 1.29 | |
| 14 | $\text{\textemdash(CH}_2\text{\textemdash C(CH}_3\text{))}_n\text{\textemdash CO}_2\text{CH(CH}_3\text{)CH}_2\text{N}^\oplus(\text{C}_2\text{H}_5)_2\text{\textemdash CH}_3\text{ Cl}^\ominus$ | 1.37 | |
| 15 | $\text{\textemdash(CH}_2\text{\textemdash C(CH}_3\text{))}_n\text{\textemdash CO}_2\text{CH}_2\text{CH}_2\text{CH}_2\text{N}^\oplus(\text{CH}_3)_2\text{\textemdash H Cl}^\ominus \quad \text{\textemdash(CH}_2\text{\textemdash CH)}_m\text{\textemdash CONH}_2$ | 2.06 | |
| 16 | $\text{\textemdash(CH}_2\text{\textemdash CH)}_n\text{\textemdash CO}_2\text{CH(CH}_3\text{)CH}_2\text{N}^\oplus(\text{C}_2\text{H}_5)_2\text{\textemdash CH}_3\text{ CH}_3\text{SO}_4^\ominus$ | 1.29 | |
| 17 | $\text{\textemdash(CH}_2\text{\textemdash CH)}_n\text{\textemdash CO}_2\text{CH}_2\text{C(CH}_3\text{)}_2\text{\textemdash N}^\oplus(\text{CH}_3)_2\text{\textemdash H Cl}^\ominus$ | 1.17 | |
| 18 | $\text{\textemdash(CH}_2\text{\textemdash C(CH}_3\text{))}_n\text{\textemdash COOCH}_2\text{CH}_2\text{N}^\oplus(\text{CH}_3)_2\text{\textemdash CH}_3\text{ Cl}^\ominus$ | 1.9 (average degree of polymerization of about 1000) | |

Table 1-continued

| Compound No. | Structural Formula | Intrinsic* Viscosity | Remarks |
|---|---|---|---|
| 19 | $-(CH_2-C(CH_3))_n-$ with $COOCH_2CH_2N^{\oplus}(CH_3)_3 \ Cl^{\ominus}$ | 6.3 (average degree of polymerization of about 4000) | |
| 20 | $-(CH_2-C(CH_3))_n-$ with $COOCH_2CH_2CH_2N^{\oplus}(CH_3)_3 \ Cl^{\ominus}$ | 11.2 (average degree of polymerization of about 8000) | |
| 21 | $-(CH_2-CH)_n-$ with $COOCH_2CH_2N^{\oplus}(C_2H_5)_2(CH_3) \ Br^{\ominus}$ | 5.1 | |
| 22 | $-(CH_2-CH)_n-$ with $COOCH_2CH_2N^{\oplus}(CH_3)_3 \ CH_3SO_4^{\ominus}$ | 3.8 | |
| 23 | $-(CH_2-C(CH_3))_n-$ with $COOCH_2CH_2N^{\oplus}(CH_3)_2 H \ Cl^{\ominus}$ | 8.5 | |
| 24 | $-(CH_2-C(CH_3))_n-$ with $COOCH_2CH_2N^{\oplus}(CH_3)_3 \ Cl^{\ominus}$ and $-(CH_2-CH)_m-$ with $CONH_2$ | 2.45 | n/m=1 |
| 25 | $-(CH_2-C(CH_3))_n-$ with $COOCH_2CH_2N^{\oplus}(CH_3)_3 \ Cl^{\ominus}$ and $-(CH_2-CH)_m-$ with 4-pyridyl·HCl | 1.58 | n/m=3/7 |
| 26 | $-(CH_2-C(CH_3))_n-$ with $COOCH_2CH_2N^{\oplus}(CH_3)_2 H \ CH_3COO^{\ominus}$ | 8.1 | |

* in 1N NaCl at 25° C.

EXAMPLE 1

Aqueous solutions containing 2,000 ppm and 1,000 ppm of each of the compounds (Nos. 1–17) indicated in Table 1 were, respectively, sprayed over potted tobacco seedlings (Xanthi nc) of leaf stages of 10–11 in an amount of 50 ml per seedling by means of a spray gun. After drying in air, each seedling was inoculated with a separately prepared purified TMV solution ($0.25 \times 10^{-6}$ g/ml) by an ordinary carborundum method and then allowed to stand in a glasshouse for 3–4 days thereby causing local lesions to form on leaves.

The number of the formed local lesions was checked for comparison with that obtained with non-treated seedlings to determine a rate of inhibiting formation of TMV lesions for each test solution.

The purified TMV solution was prepared by isolating TMV from a sap of TMV-infected leaves and purifying it by means of an ultra-centrifuge.

The test results are shown in Table 2.

Furthermore, chemical damage was observed by spraying 2,000 ppm of each of the compounds (Nos. 1–17) over tobacco seedlings (Bright Yellow) of leaf stages of 10–11, with the result that neither withering of the seedling nor chemical spot was observed.

Table 2

| Compound No. | Rate of Inhibiting Formation of TMV Lesion (%) | |
|---|---|---|
| | 2000 ppm | 1000 ppm |
| 1 | 97.3 | 89.2 |
| 2 | 94.3 | 88.4 |
| 3 | 93.7 | 88.6 |
| 4 | 96.2 | 89.7 |
| 5 | 95.4 | 90.4 |
| 6 | 95.7 | 88.7 |
| 7 | 93.8 | 86.5 |
| 8 | 95.9 | 90.1 |
| 9 | 94.0 | 91.1 |
| 10 | 95.6 | 89.4 |
| 11 | 97.1 | 92.1 |
| 12 | 96.6 | 92.3 |
| 13 | 92.1 | 86.4 |
| 14 | 90.3 | 86.9 |

Table 2-continued

| Compound No. | Rate of Inhibiting Formation of TMV Lesion (%) | |
|---|---|---|
| | 2000 ppm | 1000 ppm |
| 15 | 87.5 | 77.4 |
| 16 | 92.5 | 85.9 |
| 17 | 94.1 | 87.0 |
| non-treated | 0 | 0 |

Rate of Inhibiting Formation of TMV lesion
$= \left(1 - \dfrac{\text{Number of Lesions in Treated Seedling}}{\text{Number of Lesions in Non-treated Seedling}}\right) \times 100\ (\%)$

EXAMPLE 2

The procedure of Example 1 was repeated using the compound Nos. 18–26 except that the concentrations of the chemical solutions of each compound were 2,500 ppm and 1,250 ppm, respectively, and the purified TMV solution has a concentration of $5 \times 10^{-7}$ g/ml, thereby determining the inhibition rates of each compound at different concentrations.

The test results are shown in Table 3.

Furthermore, chemical damage was observed by spraying a solution of each of the compound Nos. 18–26 in a concentration of 2,500 ppm over tobacco seedlings (Bright Yellow) of leaf stages of 10–11, with the result that neither withering of the seedlings nor chemical spot appeared.

Table 3

| Compound No. | Rate of Inhibiting Formation of TMV Lesion (%) | |
|---|---|---|
| | 2500 ppm | 1250 ppm |
| 18 | 96.9 | 90.6 |
| 19 | 98.7 | 92.1 |
| 20 | 99.2 | 94.1 |
| 21 | 98.5 | 93.0 |
| 22 | 97.7 | 92.4 |
| 23 | 97.5 | 92.2 |
| 24 | 96.5 | 91.8 |
| 25 | 95.8 | 90.5 |
| 26 | 95.4 | 91.7 |
| Non-treated | 0 | |

Rate of Inhibiting Formation of TMV Lesion
$= \left(1 - \dfrac{\text{Number of Lesions in Treated Seedling}}{\text{Number of Lesions in Non-treated Seedling}}\right) \times 100\ (\%)$

EXAMPLE 3

Aqueous solutions of each of the compounds indicated in Table 4 with concentrations of 2,000 ppm and 1,000 ppm were each sprayed over young cowpea plants growing for 10 days after seedling (*Vigna sinenis* var. *sesguipendalis*, cv *Kurodane sanjaku*) in an amount of 5 ml per plant by means of a spray gun. After drying in air, a separately prepared CMV inoculation solution (with a concentration of $10 \times 10^{-6}$ g/ml) was inoculated into the plants by an ordinary carborundum method, followed by allowing to stand in a glasshouse for 3–4 days to cause local lesion to form on leaves of the plant. The number of the formed local lesions was checked and compared with that obtained with the non-treated plant to determine a rate of inhibiting formation of CMV lesions for each test solution.

The test results are shown in Table 4 below.

Table 4

| Compound No. | Rate of Inhibiting Formation of CMV Lesion (%) | |
|---|---|---|
| | 2000 ppm | 1000 ppm |
| 1 | 96.7 | 92.3 |
| 3 | 95.8 | 90.5 |
| 4 | 97.2 | 93.4 |
| 5 | 96.2 | 93.6 |
| 6 | 92.4 | 89.9 |
| 9 | 91.5 | 87.1 |
| 10 | 94.8 | 90.6 |
| 11 | 95.8 | 92.2 |
| 14 | 90.2 | 85.4 |
| Non-treated | 0 | 0 |

Rate of Inhibiting Formation of CMV Lesion =
$\left(1 - \dfrac{\text{Number of Lesions in Treated Plant}}{\text{Number of Lesions in Non-treated Plant}}\right) \times 100\ (\%)$

EXAMPLE 4

The compound Nos. 18–26 were tested in the same manner as in Example 3 except that the concentration of the solutions being sprayed were 2,500 ppm and 1,250 ppm, respectively, to determine the inhibition rate for CMV.

The test results are shown in Table 5 below.

Table 5

| Compound No. | Rate of Inhibiting Formation of CMV Lesion (%) | |
|---|---|---|
| | 2500 ppm | 1250 ppm |
| 18 | 95.5 | 90.1 |
| 19 | 96.7 | 89.9 |
| 20 | 99.0 | 92.7 |
| 21 | 97.7 | 91.2 |
| 22 | 98.1 | 92.3 |
| 23 | 96.8 | 90.4 |
| 24 | 96.7 | 90.6 |
| 25 | 95.0 | 89.7 |
| 26 | 96.2 | 91.3 |
| Non-treated | 0 | |

Rate of Inhibiting Formation of CMV Lesion =
$\left(1 - \dfrac{\text{Number of Lesions in Treated Plant}}{\text{Number of Lesions in Non-treated Plant}}\right) \times 100\ (\%)$

EXAMPLE 5

Tobacco seedlings of Bright Yellow to be a kind of systemic infection plant were used to examine the effect of the chemicals of the invention in a field artificially contaminated with TMV*.

Note: *A planting hole in the field in which the seedling was planted was charged with a soil which had been mixed with dry powder of tobacco leaves attacked with TMV in an amount of 0.5 per l of the soil.

Aqueous solution having a concentration of 2,000 ppm of the compound Nos. 4, 8, 9 and 13 indicated in Table 1 were each sprayed over the tobacco seedlings by means of a sprayer of a knapsack type in an amount of 50 ml per seedling. After drying in air, the sprayed seedlings were planted in the contaminated field.

14 days, 21 days and 28 days after the planting, the seedlings were observed to check how many seedlings were infected with the mosaic disease.

The test results are shown in Table 6 below.

Table 6

| Compound No. | Infected Seedlings/Total of Seedlings | | |
|---|---|---|---|
| | 14 days | 21 days | 28 days |
| 4 | 0/15 | 1/15 | 3/15 |
| 8 | 2/15 | 4/15 | 5/15 |
| 9 | 0/15 | 1/15 | 2/15 |
| 13 | 1/15 | 3/15 | 5/15 |
| Non-treated | 12/15 | 15/15 | 15/15 |

EXAMPLE 6

Potted tobacco seedlings Bright Yellow to be a kind of systemic infection plant were used to examine the effect of the chemicals of the invention.

Aqueous solutions containing 2,500 ppm of the compound Nos. 19, 20, 21 and 24 indicated in Table 1 were each sprayed over the tobacco seedlings by means of a spray gun. After drying in air, the purified TMV solution having a TMV concentration of $2 \times 10^{-7}$ g/ml was inoculated in the largest leaf of each of the seedlings in a size of $5 \times 5$ cm, followed by allowing to stand in a glasshouse.

The seedlings which shows symptoms of the mosaic disease was regarded as infected seedlings. 14 days, 21 days and 28 days after the inoculation, the infected condition was observed with the results shown in Table 7 below.

Table 7

| Compound No. | Infected Seedlings/Total of Inoculated Seedlings | | |
|---|---|---|---|
| | 14 days | 21 days | 28 days |
| 19 | 0/15 | 1/15 | 3/15 |
| 20 | 0/15 | 0/15 | 2/15 |
| 21 | 0/15 | 2/15 | 3/15 |
| 22 | 1/15 | 2/15 | 3/15 |
| non-treated | 14/15 | 15/15 | 15/15 |

EXAMPLE 7

Tomato seedlings (kind: Yuyake) were used to examine the effect of the chemicals of the invention in a field artificially contaminated with TMV.

An aqueous solution containing 2,000 ppm of each of the compounds corresponding to Nos. 4, 8, and 10 indicated in Table 1 was applied to the seedlings, prior to planting, in an amount of 50 ml per seedling and also to the planting hole in an amount of 500 ml by means of a sprayer of a knapsack type. After drying the seedlings in air, the seedlings were each planted in the hole. About 1 month after the planting, the seedlings which were infected with the mosaic disease were checked. The test results are shown in Table 8.

Note: The hole was charged with a soil which was mixed with a dry powder of tomato leaves attacked with TMV in an amount of 0.5 g per l of the soil.

Table 8

| Compound No. | Infected Seedlings/Total of Seedlins | Preventive value(%) |
|---|---|---|
| 4 | 2/20 | 90.0 |
| 8 | 4/20 | 80.0 |
| 10 | 4/20 | 80.0 |
| non-treated | 20/20 | 0 |

Preventive Value = $(1 - \frac{\text{Number of Infected Seedlings in treated case}}{\text{Number of Infected Seedlings in non-treated case}}) \times 100\ (\%)$

EXAMPLE 8

The procedure of Example 7 was repeated using an aqueous solution containing 2,500 ppm of each of the compound Nos. 19, 24 and 25 indicated in Table 1. The test results are shown in Table 9 below.

Table 9

| Compound No. | Infected Seedlings/Total of Seedlings | Preventive Value(%) |
|---|---|---|
| 19 | 1/20 | 94.1 |
| 24 | 2/20 | 88.2 |
| 25 | 2/20 | 88.2 |
| non-treated | 17/20 | 0 |

Preventive Value = $(1 - \frac{\text{Number of Infected Seedlings in Treated Case}}{\text{Number of Infected Seedings in non-treated case}}) \times 100\ (\%)$

What is claimed is:

1. A method for controlling viral diseases in plants comprising applying to the plants an effective amount of (A) a homopolymer of a compound expressed by the general formula

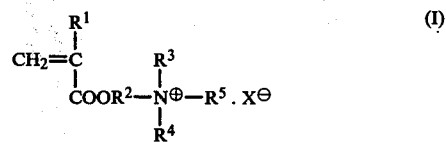

(I)

wherein $R^1$ represents a hydrogen atom or a methyl group, $R^2$ represents a linear or a branched alkylene group containing from 2 to 5 carbon atoms, $R^3$ and $R^4$ independently represent a lower alkyl group, $R^5$ represents a hydrogen atom or a lower alkyl group, and X represents a halogen atom, a nitric acid radical, sulfuric acid radical, lower fatty acid radical or a lower alkylsulfuric acid radical or (B) a copolymer of the compound expressed by the above formula (I) and at least one ethylenically unsaturated monomer copolymerizable with said compound.

2. A method according to claim 1, wherein $R^1$ represents a hydrogen atom or a methyl group, $R^2$ represents a dimethylene group, a trimethylene group or a tetramethylene group, $R^3$ and $R^4$ independently represent an alkyl group containing from 1 to 3 carbon atoms, and $R^5$ represents a hydrogen atom or an alkyl group containing from 1 to 3 carbon atoms.

3. A method according to claim 1, wherein $R^1$ represents a hydrogen atom or a methyl group, $R^2$ represents an ethylene group having at least one methyl group at the side chain thereof, $R^3$ and $R^4$ independently represent an alkyl group containing from 1 to 3 carbon atoms, and $R^5$ represents a hydrogen atom or an alkyl group containing from 1 to 3 carbon atoms.

4. A method according to claims 2 or 3 wherein $R^5$ represents a hydrogen atom and X represents a chlorine atom, a bromine atom, an iodine atom, nitric acid radical, sulfuric acid radical or a lower fatty acid radical.

5. A method according to claims 2 or 3, wherein $R^5$ represents an alkyl group containing from 1 to 3 carbon atoms and X represents a chlorine atom, a bromine atom, a iodine atom or an alkylsulfuric acid radical containing from 1 to 3 carbon atoms in the alkyl moiety thereof.

6. A method according to claim 1, wherein said ethylenically unsaturated monomer is a nonionic monomer selected from the group consisting of a lower alkyl ester of acrylic acid or methacrylic acid, acrylamide, methacrylamide, vinylpyrrolidone, acrylonitrile, methacrylonitrile, vinyl acetate, vinyl methyl ether, vinyl ethyl ether, ethylene and isobutylene.

7. A method according to claim 6, wherein said ethylenically unsaturated monomer is acrylamide or methacrylamide.

8. A method according to claim 1, wherein said ethylenically unsaturated monomer is a cationic monomer selected from the group consisting of vinyl pyridine and p-dimethylaminomethylstyrene.

9. A method according to claim 1, wherein the intrinsic viscosity of said homopolymer or said copolymer is in the range of from 0.3 to 15.

10. A method according to claim 1, wherein the content of said compound expressed by the general formula (I) in the copolymer is in the range of above 10 mole %.

11. A method according to claim 1, wherein the plant virus is tobacco mosaic virus, cucumber mosaic virus, cucumbers green mottle mosaic virus, potato X virus, lettuce mosaic virus or melon necrotic spot virus.

12. A method according to claim 11, wherein the plant virus is tobacco mosaic virus, cucumber mosaic virus or cucumber green mottle mosaic virus.

13. A method according to claim 1, wherein the plant is Solanaceae, Cucurbitaceae, Leguminosae, Cruciferceae or Rosaceae.

14. A method according to claim 1, wherein the plant is Solanaceae such as tobacco, tomato and green pepper, or Cucurbitaceae such as cucumber, watermelon and melon.

15. A method according to claim 14, wherein the plant is tomato or tobacco.

16. The method of claim 1 wherein there is applied a wettable powder comprising 70–99 parts by weight of the homopolymer or copolymer of claim 1, and 1–30 parts by weight of a surface active agent.

17. The method of claim 1 wherein there is applied an emulsion or solution comprising 10–60 parts by weight of the homopolymer or copolymer of claim 1, 20–90 parts by weight of a solvent, and 1–20 parts by weight of a surface active agent.

18. The method of claim 1 wherein there is applied a dust comprising 1–20 parts by weight of the homopolymer or copolymer of claim 1, 80–98 parts by weight of a carrier, and 1–5 parts by weight of a surface active agent.